United States Patent [19]

Sunshine et al.

[11] Patent Number: 4,906,625

[45] Date of Patent: Mar. 6, 1990

[54] ANALGESIC AND ANTI-INFLAMMATORY COMPOSITIONS COMPRISING DIPHENHYDRAMINE AND METHODS OF USING SAME

[75] Inventors: Abraham Sunshine, New York; Eugene M. Laska, Larchmont; Carole E. Siegel, Mamaroneck, all of N.Y.

[73] Assignee: Richardson-Vicks, Inc., Wilton, Conn.

[21] Appl. No.: 180,570

[22] Filed: Apr. 12, 1988

Related U.S. Application Data

[62] Division of Ser. No. 41,692, Apr. 23, 1987, Pat. No. 4,755,532, which is a division of Ser. No. 856,414, Apr. 28, 1983, Pat. No. 4,683,243, which is a division of Ser. No. 711,525, Mar. 14, 1985, Pat. No. 4,585,783, which is a division of Ser. No. 578,288, Feb. 19, 1984, Pat. No. 4,522,826.

[51] Int. Cl.$^4$ .............................................. A61K 31/54
[52] U.S. Cl. .................................................. 514/226.5
[58] Field of Search .......................................... 514/222

[56] References Cited

U.S. PATENT DOCUMENTS

| | | | |
|---|---|---|---|
| 3,167,475 | 1/1965 | Gottfried et al. | 514/282 |
| 4,322,427 | 3/1982 | Buyniski et al. | 514/282 |
| 4,379,789 | 4/1983 | Capetola et al. | 514/282 |

FOREIGN PATENT DOCUMENTS

| | | |
|---|---|---|
| 194061 | 4/1976 | Austria . |
| 0030092 | 2/1985 | European Pat. Off. . |
| 2544100 | 10/1975 | Fed. Rep. of Germany . |
| 4848M | 2/1967 | France . |
| 1042637 | 9/1966 | United Kingdom . |

OTHER PUBLICATIONS

Rote Liste 1977/78; 71 021 B.
Lear et al, "Comparative Studies of Tranquilizers Used in Anesthesia," JAMA 1958, 166(12): 1438-1443.
Cappe, B. E. et al, "Recent Advances in Obstetric Analgesic," JAMA 1954, 154(5): 377-379.
Compos, V. M. et al, "The Analgesic and Hypothermic Effects of Nefopam, Morphine, Aspirin, Diphenhydramine and Placebo", Journal of Clin. Pharmocology, Jan., 1980, pp. 42-49.
Albal, M. V. and Chandorka, A. G., "Clinical Evaluation of Sedyn-a-Forte, an Analgesic Injection Containing Analgin, DIphenhydramine and Diazepam," Indian Journal of Ophthalmology, 1982, 30:271-273.
Beaver, W. T. and Feise, G., "Comparison of the Analgesic Effects of Morphine, Hydroxyzine, and Their Combination in Patents with Postoperative Pain," Advances in Pain Research and Therapy, 1976, 1:553-557.
Bluhm, et al, "Potentiation of Opioid Analgesia by $H_1$ and $H_2$ Antagonists," Life Sciences, 1982, 31:1229-1232.

Primary Examiner—Stanley J. Friedman
Attorney, Agent, or Firm—Burns, Doane, Swecker & Mathis

[57] ABSTRACT

Novel pharmaceutical compositions of matter are provided comprising analgesic/non-steroidal anti-inflammatory drugs and diphenhydramine and methods of using said compositions to elicit and enhanced analgesic and/or anti-inflammatory response in mammalian organisms in need of such treatment.

29 Claims, 1 Drawing Sheet

1

ANALGESIC AND ANTI-INFLAMMATORY COMPOSITIONS COMPRISING DIPHENHYDRAMINE AND METHODS OF USING SAME

CROSS-REFERENCE TO RELATED APPLICATIONS

This application is a division of application Ser. No. 041,692, filed Apr. 23, 1987, now U.S. Pat. No. 4,755,532; which is a division of Ser. No. 856,414, filed Apr. 28, 1983, now U.S. Pat. No. 4,683,243; which is a division of Ser. No. 711,525, filed Mar. 14, 1985, now U.S. Pat. No. 4,585,783; which is a division of Ser. No. 578,288, filed Feb. 8, 1984, now U.S. Pat. No. 4,522,826.

BACKGROUND OF THE INVENTION

The present invention relates generally to novel pharmaceutical compositions of matter comprising diphenhydramine and one or more non-steroidal anti-inflammatory drugs (NSAID) having analgesic and anti-inflammatory properties, and to methods of using said compositions to elicit an enhanced analgesic or anti-inflammatory response in mammalian organisms in need of such treatment.

Non-narcotic analgesics, most of which are also known as non-steroidal anti-inflammatory drugs (NSAID), are widely administered orally in the treatment of mild to severe pain. Within this class, the compounds vary widely in their chemical structure and in their biological profiles as analgesics, anti-inflammatory agents and antipyretic agents. Aspirin, acetaminophen and phenacetin have long been among the most commonly used members of this group; more recently, however, a large number of alternative non-narcotic agents offering a variety of advantages over the earlier drugs have been developed. Tolerance or addiction to these drugs is not generally a problem with their continuous use in the treatment of pain or in the treatment of acute or chronic inflammatory states (notably, rheumatoid arthritis and osteoarthritis); nevertheless, these drugs generally have a higher potential for adverse side-effects at the upper limits of their effective dose ranges. Moreover, above each drug's upper limit or ceiling, administration of additional drug does not usually increase the analgesic or anti-inflammatory effect. Among the newer compounds in the non-narcotic analgesic/nonsteroidal anti-inflammatory group are compounds such as diflunisal (Dolobid®), zomepirac sodium (Zomax®), ibuprofen (Motrin®), naproxen (Naprosyn®), fenoprofen (Nalfon®), piroxicam (Feldene®), flurbiprofen, mefenamic acid (Ponstel®) and sulindac. See also *Physicians' Desk Reference*, 35th edition, 1981, and *The Merck Index*, ninth edition, Merck & Co., Rahway, N.J. (1976), for information on specific nonsteroidal anti-inflammatory agents. Also see, generally, Wiseman, "Pharmacological Studies with a New Class of Nonsteroidal Anti-Inflammatory Agents—The Oxicams—With Special Reference to Piroxicam (Feldene®), *The American Journal of Medicine*, Feb. 16, 1982: 2–8; Foley et al, *The Management of Cancer Pain, Volume II—The Rational Use of Analgesics in the Management of Cancer Pain*, Hoffman-LaRoche Inc., 1981; and *Cutting's Handbook of Pharmacology*, sixth edition, ed. T. Z. Czaky, M. D., Appleton-Century-Crofts, New York, 1979, Chapter 49: 538–550, including structural formulas for representative group members.

Diphenhydramine[2-(diphenylmethoxy)-N,N-dimethylethylamine] is also a well-known therapeutic agent in long standing use by clinicians as an antihistamine. It is recognized in both the U.S.P. and N.F. as an official antihistamine of the ethanolamine (or aminoalkyl ether) type and is available as the hydrochloride salt in Benadryl® and various alternative sources in 50 milligram delayed action tablets, 25 and 50 milligram capsules, elixirs (12.5 mg/5 ml) and sterile solution for injection (10 mg/ml). Depending upon the therapeutic indication, diphenhydramine is recommended in single or divided doses of between 12.5 to 50 milligrams with a maximum daily dosage not to exceed 300 milligrams. The antihistaminic activity of diphenhydramine is directly attributable to its competition with histamine for cell receptor sites on effector cells although diphenhydramine also demonstrates, in addition, a number of therapeutic applications attributable to central actions unrelated to histamine antagonism. Antihistaminic indications for diphenhydramine include perennial and seasonal allergic rhinitis, vasomotor rhinitis, allergic conjunctivitis, urticaria and as adjunctive therapy for anaphylactic reactions. Central nervous system side effects (non-histaminic actions) which have been capitalized upon include prophylactic and active treatment of motion sickness and, more broadly, as an anti-nauseant and in the treatment of mild forms of Parkinsonism. Diphenhydramine demonstrates both stimulant and depressant effects on the central nervous system although stimulation is only occasionally seen in patients given conventional doses with accompanying restlessness, nervousness and inability to sleep. The more predominant sedative action of diphenhydramine has been beneficially capitalized upon the usage of the diphenhydramine as a somnolent when employed at the maximum 50 milligrams dose in both prescription and over-the-counter forms. In this regard, it is noted that the Food and Drug Administration announced in the November 1983 FDA Drug Bulletin (Vol. 13, No. 3) that diphenhydramine (50 mg.) may now be marketed over-the-counter as a nighttime sleep aid.

An early study (1958) investigated the properties of diphenhydramine as a pre-anesthetic medication. (Lear, et al., "Comparative Studies of Tranquilizers Used in Anesthesia." *JAMA*, 1958, 166 (12): 1438–1443). The authors concluded that diphenhydramine, particularly when used in combination with meperidine, provides beneficial preoperative sedation with less overall depression than previously experienced with the use of routine doses or narcotics and barbiturates.

Diphenhydramine has also been investigated with varying results with respect to its potential as a weak analgesic. Diphenhydramine hydrochloride when introduced intravenously has been reported as being useful in obstetric analgesia alone and in combination with alcohol. See Cappe, B. E. et al, "Recent Advances in Obstetric Analgesia", *JAMA*, 1954, 154 (5): 377–379. Campos et al in a comparative study found that diphenhydramine given either orally or intramuscularly could not be distinguished from placebo in patients with postoperative fractures of somatic pain. ["The Analgesic and Hypothermic Effects of Nefopam, Morphine, Aspirin, Diphenhydramine and Placebo", *Journal of Clin. Pharmacology*, January, 1980, pp. 42–49.]

Albal and Chandorkar studied an injectable combination analgesic consisting of analgin 375 mg, a centrally acting analgesic, diazepam 2.5 mg, and diphenhydramine 20 mg, and found relief from pain. They did not, however, study the unique contribution of diphenhydramine. [Albal, M. V., and Chandorkar, A. G. "Clinical Evaluation of Sedyn-a-Forte, an Analgesic Injection Containing Analgin, Diphenhydramine and Diazepan." *Indian Journal of Ophthalmology*, 1982, 30: 271–273]. [Note: analgin referred to in the foregoing study in dypyrone; see *The Merck Index*, p. 3361, 1976.]

While diphenhydramine has been investigated with respect to its weak analgesic properties, it is also evident from the foregoing that its sedative and local anesthetic properties may, in part, account for its suspected potential for relieving pain. In the Lear et al, supra, study diphenhydramine at 25 to 50 milligram doses were insufficient as a preanesthetic medication and combination with meperidine (a narcotic analgesic) was proposed to optimize the potential beneficial effects of diphenhydramine as an analgesic.

Hydroxyzine, which is a minor tranquilizer with antihistaminic activity, has been evaluated as an analgesic. Beaver and Feise found that, "This study unequivocally demonstrates analgesic activity for a 100 mg dose of intramuscular hydroxyzine in the general range of that produced by 8 mg of morphine. In addition, the analgesic activity of hydroxyzine appears additive with that of morphine when the two drugs are given together." The findings of the study do not indicate synergistic activity. (Beaver, W. T. & Feise, G. "Comparison of the Analgesic Effects of Morphine, Hydroxyzine, and Their Combination in Patients with Postoperative Pain." *Advances in Pain Research and Therapy*, 1976, 1: 553–557)

Only recently have animal studies been conducted in which the analgesic activity of diphenhydramine has been investigated. Bluhm, et al., in a study conducted on mice, found that diphenhydramine potentiates morphine, a centrally acting drug, when administered parenterally. Oral administration of drugs was not studied. (Bluhm, et al., "Potentiation of Opioid Analgesia By $H_1$ and $H_2$ Antagonists." *Life Sciences*, 1982, 31: 1229–1232)

Diphenhydramine has not been heretofore proposed for use in combination with any of the newer nonsteroidal analgesic/anti-inflammatory agents (i.e., excluding aspirin, acetaminophen and phenacetin). In U.S. Pat. No. 4,420,483 issued Dec. 13, 1983, the present applicants disclose the hastening of the onset of analgesic and anti-inflammatory responses observed with several different nonsteroidal anti-inflammatory agents as well as the enhancement of the analgesic and anti-inflammatory response with such agents by the concomitant administration of caffeine as a potentiating adjuvant.

Applicants have now surprisingly found that diphenhydramine synergistically enhances the analgesic and anti-inflammatory properties of such non-steroidal anti-inflammatory drugs (NSAID).

SUMMARY OF THE INVENTION

It is, therefore, a primary object of the present invention to provide a novel pharmaceutical composition of matter for promoting an enhanced analgesic and anti-inflammatory response in a mammalian organism in need of such treatment comprising an analgesically and anti-inflammatorily effective amount of a non-steroidal anti-inflammatory drug (NSAID) in combination with diphenhydramine or a pharmaceutically acceptable salt thereof.

It is a further object of the present invention to provide methods for obtaining analgesic and anti-inflammatory responses in mammals, including humans, by the administration of preselected dosages of a non-steroidal anti-inflammatory agent, with diphenhydramine.

A still further object of the present invention is to provide a pharmaceutical composition of matter for obtaining a synergistic analgesic and anti-inflammatory response in mammals in which the composition comprises an analgesically and anti-inflammatorily effective amount of a selected NSAID and a synergistic amount of diphenhydramine optionally in the presence of a pharmaceutically acceptable inert carrier.

Another object of the invention is to provide suitable dosage unit forms of one or more NSAID's and diphenhydramine adapted for, e.g., oral, rectal, parenteral, topical, etc., administration and useful in the treatment, management and mitigation of pain and/or inflammation.

These and other similar objects, advantages and features are accomplished according to the products, compositions and methods of the invention comprised of a non-steroidal anti-inflammatory drug or analgesic and diphenhydramine and analgesic and anti-inflammatory methods employing same.

BRIEF DESCRIPTION OF THE DRAWING

The FIGURE of Drawing is a plot of dose of diphenhydramine versus dose of ibuprofen in the phenylquinone writhing assay to indicate the number of mice protected.

DESCRIPTION OF THE PREFERRED EMBODIMENTS

Figure 1:
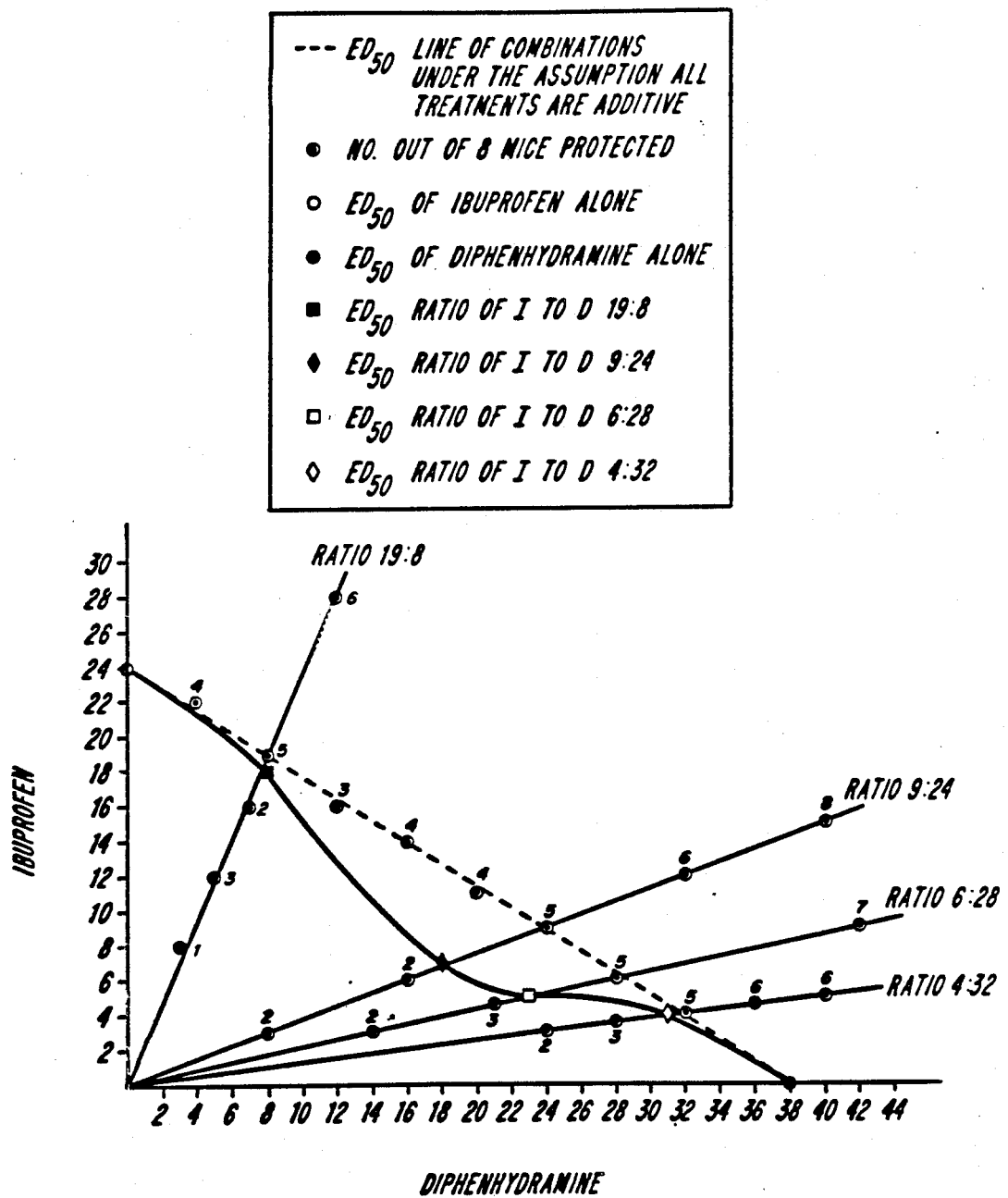

It has now been unexpectedly found in accordance with the present invention that the analgesic and anti-inflammatory effects observed upon the administration of a non-narcotic analgesically active non-steroidal anti-inflammatory drug (i.e., analgesic/NSAID), can be synergistically enhanced by the co-administration of diphenhydramine or a non-toxic pharmaceutically acceptable salt thereof.

As used herein, the terms "synergism" and "synergistic" are used to describe the potentiated analgesic and anti-inflammatory responses elicited by the co-administration of an analgesic NSAID and diphenhydramine (or pharmaceutically acceptable salts thereof). More specifically, these terms as used herein are defined in contradistinction to merely additive effects. The effects of two compounds are additive if the response to a dose of both in combination does not change when a portion of one component is removed from the mixtures and replaced by an equipotent portion of the other. If such substitution increases the response, the mixing together of the compounds is said to potentiate their effects and synergism exists.

The non-narcotic analgesics/nonsteroidal anti-inflammatory drugs for use in the compositions and methods of the present invention can be selected from the following categories:

(1) the propionic acid derivatives;
(2) the acetic acid derivatives;
(3) the fenamic acid derivatives;
(4) the biphenylcarboxylic acid derivatives; and
(5) the oxicams.

The term "selected NSAID" as used herein is intended to mean any non-narcotic analgesic/non-steroidal anti-inflammatory compound falling within one of the five structural categories above but excluding aspirin, acetaminophen and phenacetin.

While some of these compounds are primarily used at the present time as anti-inflammatory agents and others are primarily used as analgesics, in fact all of the contemplated compounds have both analgesic and anti-inflammatory activity and can be used at appropriate dosage levels for either purpose in the compositions and methods of the present invention. The compounds in groups (1) through (4) typically contain a carboxylic acid function; however, those acids are sometimes administered in the form of their pharmaceutically acceptable acid addition or alkali metal salts, e.g., sodium salts.

The propionic acid derivatives for use herein include, but are not limited to, ibuprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be encompassed by this group. Presently preferred members of the propionic acid group include ibuprofen, naproxen, flurbiprofen, fenoprofen, ketoprofen and fenbufen.

Thus, "propionic acid derivatives" as defined herein are non-narcotic analgesics/nonsteroidal anti-inflammatory drugs having a free —CH(CH$_3$)COOH or —CH$_2$CH$_2$COOH group (which optionally can be in the form of a pharmaceutically acceptable salt group, e.g. —CH(CH$_3$)COO$^-$Na$^+$ or —$CH_2$CH$_2$COO$^-$Na$^+$), typically attached directly or via a carbonyl function to a ring system, preferably to an aromatic ring system.

The acetic acid derivatives for use herein include, but are not limited to, indomethacin, sulindac, tolmetin, zomepirac, diclofenac, fenclofenac, alclofenac, ibufenac, isoxepac, furofenac, tiopinac, zidometacin, acemetacin, fentiazac, clidanac and oxpinac. Structurally related acetic acid derivatives having similar analgesic and anti-inflammatory properties are also intended to be encompassed by this group. Presently preferred members of the acetic group include tolmetin sodium, zomepirac sodium, sulindac and indomethacin.

Thus, "acetic acid derivatives" as defined herein are non-narcotic analgesics/nonsteroidal anti-inflammatory drugs having a free —CH$_2$COOH group (which optionally can be in the form of a pharmaceutically acceptable salt group, e.g., —CH$_2$COO$^-$Na$^+$), typically attached directly to a ring system, preferably to an aromatic or heteroaromatic ring system.

The fenamic acid derivatives for use herein include, but are not limited to, mefenamic acid, meclofenamic acid, flufenamic acid, niflumic acid and tolfenamic acid. Structurally related fenamic acid derivatives having similar analgesic and anti-inflammatory properties are also intended to be encompassed by this group. Presently preferred members of the fenamic acid group include mefenamic acid and meclofenamate sodium (meclofenamic acid, sodium salt).

Thus, "fenamic acid derivative" as defined herein are non-narcotic analgesics/nonsteroidal anti-inflammatory drugs which contain the basic structure

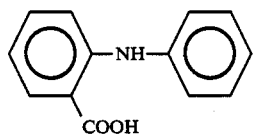

which can bear a variety of substituents and in which the free —COOH group can be in the form of a pharmaceutically acceptable salt group, e.g., —COO$^-$Na$^+$.

The biphenylcarboxylic acid derivatives for use herein include, but are not limited to, diflunisal and flufenisal. Structurally, related biphenylcarboxylic acid derivatives having similar analgesic and anti-inflammatory properties are also intended to be encompassed by this group. Preferred members of this group are diflunisal and flufenisal.

Thus, "biphenylcarboxylic acid derivative" as defined herein are non-narcotic analgesics/nonsteroidal anti-inflammatory drugs which contain the basic structure

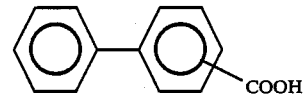

which can bear a variety of substituents and in which the free —COOH group can be in the form of a pharmaceutically acceptable salt group, e.g. —COO$^-$Na$^+$.

The oxicams for use herein include, but are not limited to, piroxicam, sudoxicam, isoxicam and CP-14,304. Structurally related oxicams having similar analgesic and anti-inflammatory properties are also intended to be encompassed by this group. A preferred member of this group is piroxicam.

Thus, "oxicams" as defined herein are non-narcotic analgesics/nonsteroidal anti-inflammatory drugs which have the general formula

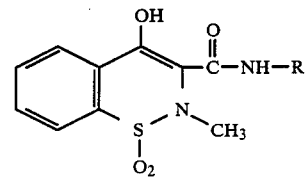

wherein R is an aryl or heteroaryl ring system.

The precise amount of non-narcotic analgesic/nonsteroidal anti-inflammatory drug for use in the present compositions will vary depending, for example, on the specific drug chosen, the dosage form thereof, i.e., standard versus sustained release, the condition for which the drug is administered and the size and kind of the mammal. Typical effective doses of the non-narcotic analgesic/nonsteroidal anti-inflammatory drugs include about 100 mg to 400 mg of propionic acid derivatives, about 25 mg to 200 mg of acetic acid derivatives, about 125 mg to 250 mg of fenamic acid derivatives, about 125 mg to 500 mg of biphenyl-carboxylic acid derivatives and about 10 mg to 20 mg of oxicam.

For humans, typical effective analgesic/anti-inflammatory amounts of presently preferred NSAIDs for use in unit dose compositions of the invention are about 125 to 500 mg diflunisal, about 25 to 100 mg zomepirac sodium, about 50 to 400 mg ibuprofen, most preferably 100–400 mg, about 125 to 500 mg naproxen, about 25 to 50 mg flurbiprofen, and about 50 to 200 mg fenoprofen, about 10 to 20 mg piroxicam, about 125 to 250 mg mefenamic acid, about 100 to 400 mg fenbufen or about 25 to 50 mg ketoprofen; however, greater or lesser amounts can be employed if desired.

For example, in one preferred embodiment of this invention, the desired therapeutic response for ibuprofen therapy in mild to moderate pain is generally observed at 200 to 600 milligrams of ibuprofen every 4 to 6 hours as necessary up to about 2400 milligrams total daily dose. Consistent with the synergistic results achieved with the ibuprofen/diphenhydramine compositions and methods of the present invention, the desired analgesic and/or anti-inflammatory response can be achieved upon the administration of ibuprofen and diphenhydramine wherein the ibuprofen component can be administered at reduced levels of between about 50 to 400 milligrams of ibuprofen and, most preferably, 100 to 400 milligrams. Alternatively, the usual dosage regimen for ibuprofen may be followed when the composition of the present invention additionally comprising diphenhydramine is employed whereby the levels of analgesia and anti-inflammatory results are enhanced.

The amount of diphenhydramine present in the compositions according to the present invention ranges between about 12.5 to 50 milligrams and, preferably, between about 25 to 50 milligrams.

In any event, the amounts of NSAID and diphenhydramine to be administered in a total daily dose should not exceed the generally recognized as safe limits established for the particular NSAID and diphenhydramine when administered alone for their respective usual therapeutic indications.

In the compositions and methods of the invention, an NSAID and diphenhydramine may be co-administered in the same composition or concomitantly administered separately.

In accordance with the practices of the present invention, the NSAID/diphenhydramine compositions may be administered in admixture with suitable pharmaceutical diluents, carriers or other excipients (collectively referred to as "carrier" materials) suitably selected with respect to the intended route of administration and conventional pharmaceutical practices. For instance, for oral administration in the form of tablets or capsules, the active drug components may be combined with any oral non-toxic pharmaceutically acceptable inert carrier such as lactose, starch, sucrose, cellulose, magnesium stearate, dicalcium phosphate, calcium sulfate, mannitol and the like. Moreover, when desired or necessary, suitable binders, lubricants, disintegrating agents and coloring agents can also be incorporated in the mixture. Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, etc. Disintegrators include, without limitation, starch, methylcellulose, agar, bentonite, guar gum, etc. Sweetening and flavoring agents and preservatives can also be included where appropriate. Similarly, injectable dosage units may be utilized to accomplish intravenous, intramuscular or subcutaneous administration and, for such parenteral administration, suitable sterile aqueous or non-aqueous solutions or suspensions, optionally containing appropriate solutes to effectuate isotonicity, will be employed.

Moreover, in accordance with another preferred embodiment of the present invention, where therapeutic indications warrant, such as in the case where the level of pain and inflammation associated with the disorder may interfere with normal sleep latency and maintenance dosage regimens may be contemplated, the NSAID/diphenhydramine compositions of the invention may be formulated for administration at bedtime as an analgesically and anti-inflammatory effective nighttime sleep aid. Accordingly, the NSAID and diphenhydramine components of the composition may be formulated in dosage unit form to provide a dose of diphenhydramine (compared to the amount necessary to promote the desired synergistic response) to take advantage of the sleep-inducing side effect of diphenhydramine.

In another preferred embodiment, the advantageous analgesic and anti-inflammatory compositions of the invention may be formulated in sustained release form to provide the rate controlled release of either or both of the components to optimize analgesic and anti-inflammatory response while minimizing undesirable side effects in, for example, patients unusually sensitive to either or both of the active drugs. Suitable dosage forms for sustained release include layered tablets containing layers of varying disintegration rates or controlled release polymeric matrices impregnated with the active components and shaped in tablet form or capsules containing such impregnated or encapsulated porous polymeric matrices. Thus, with respect to such layered tablets, one layer may contain an initial dosing amount of, for example, ibuprofen, of 400 milligams and 25 milligrams of diphenhydramine, whereas two or more further layers may contain, for instance, 100 milligrams of ibuprofen and 15 to 25 milligrams of diphenhydramine to be released serially every 4 to 6 hours consistent with the normal dosage schedule. Another advantage afforded the analgesic and anti-inflammatory compositions of the present invention by the inclusion of the diphenhydramine component is that gastrointestinal disturbances, which are the most frequent adverse reactions reported for non-steroidal anti-inflammatory drugs, including complaints involving abdominal distress, epigastric pain, indigestion, nausea and vomiting may often be minimized or, at least, reduced. The foregoing advantage is both a function of the synergism exhibited by the NSAID/diphenhydramine composition which allows for the use of the NSAID component in quantities substantially less than dosages presently considered necessary as an analgesic or anti-inflammatory agent in humans, which lower doses result in lowering the incidence or severity of undesirable side effects, as well as the presence of diphenhydramine contributing valuable antinauseant and antiemetic properties to the composition.

In patients particularly susceptible to the tendency of either the NSAID or diphenhydramine to promote drowsiness or, in the extreme, sedation and, otherwise, in ambulatory patients where drowsiness and/or sedation may represent untoward side effects, the compositions of the present invention may further include caffeine to counteract drowsiness symptoms and to further take advantage of the potentiated analgesic and anti-inflammatory response effectuated by the addition of caffeine as disclosed in applicants U.S. Pat. No. 4,420,483.

EXAMPLE 1

Pharmacologic Test for Synergism

Ibuprofen/Diphenhydramine

The unexpected synergistic analgesic effect of the addition of diphenhydramine to ibuprofen is evidenced by tests conducted on mice. Blue Spruce Farm male mice weighing 18-28 grams at the time of testing are used throughout. All mice are dosed orally by gavage with ibuprofen and/or diphenhydramine. The formulation of each test article is a solution or suspension in 0.25% methylcellulose manufactured by Fisher Scientific Company. A dosing volume of 10 ml/mg is used. All doses are coded and the test is performed under a code not known to the observer. Doses are based upon the weights of the animal taken prior to dosing.

METHOD

A phenylquinone writhing assay in mice was conducted over a four day period to test for synergism of the analgesic activity of ibuprofen and diphenhydramine.

The assay consists of phenyl-p-benzoquinone (PPQ) introduced in mice thirty minutes post dose of the test treatment(s). The PPQ is prepared as a 0.02% aqueous solution in 5 ml ethyl alcohol q.s. to 100 ml with distilled water and is administered intraperitoneally at 0.25 ml/mouse. The mice are injected with the PPQ solution and are placed in individual plastic squares 4"×4"×5" deep and observed for a ten minute period post treatment dose for exhibition of the writhing syndrome. Complete blocking of the writhing syndrome for the ten minute observation period in any one mouse is considered a positive response for that mouse. Conversely, if the mouse definitely writhes at least once, it is considered to be not protected from the PPQ.

Three hundred twenty-eight mice were randomly assigned to 40 groups. Two groups of ten mice per series were assigned to a control group (10 prior to the administration of the test treatments and 10 post administration) to verify the ability of the solutions to produce the writhing response.

The purpose of the assay on the first day is to estimate the $ED_{50}$ (effective dose in 50% of treated mice) of ibuprofen alone and of diphenhydramine alone, and to estimate the relative potency, $\rho$, of ibuprofen to diphenhydramine, determined as the ratio of the $ED_{50}$ of ibuprofen to the $ED_{50}$ of diphenhydramine. Eight mice per group are dosed orally (via intubation) with 2, 5, 10 and 20 mg/kg of ibuprofen and 5, 10, 20 and 50 mg/kg of diphenyhydramine. Table 1 shows the number of mice protected from writhing activity for each dose of ibuprofen and diphenhydramine. The method of Finney ["Statistical Method of Biological Assay", McMillan Pub., 3rd Edition, 1978] is used to estimate the $ED_{50}$'s of ibuprofen alone and diphenhydramine alone.

On the second day eight combination doses were studied. The doses were chosen based upon the $ED_{50}$'s established in the preceding day's experiment, which, under the assumption of additivity, would provide protection for 50% of the mice. These doses were tested in order to observe those ratio(s) of the combination drugs that would yield a synergistic effect. Combinations for which five or more mice exhibit blockage of writhing are candidates for further study. The doses of the constituent drugs in mg/kg for the eight groups were for ibuprofen (I) and diphenhydramine (D) respectively, [abbreviated as (I,D)]: (22,4), (19,8), (16,12), (14,6), (11,20), (9,24), (6,28), (4,32). Table 2 shows for each of these combination doses, the number of mice protected from writhing activity.

On the third and fourth days the four specific fixed ratios that achieved 5 or more protected mice were studied in more detail, i.e., the first combination treatment used a ratio of ibuprofen to diphenhydramine of 19:8 and the doses of the constituent drugs in mg/kg that were studied were (8,3), (12,5), (16,7) and (28,12). The second combination treatment used a ratio of doses of ibuprofen to diphenhydramine of 6:28 and the doses of the constituent drugs in mg/kg that were studied were (3,14), (4.5,21) and (9,42). The third combination treatment used a ratio of doses of ibuprofen to diphenhydramine of 9:24 and the doses of the constituent drugs in mg/kg that were studied were (3,8), (6,16), (12,32) and (15,40). The fourth combination treatment used a ratio of doses of ibuprofen to diphenhydramine of 4:32 and the doses of the constituent drugs in mg/kg that were studied were (3,24), (3.5,28) (4.5,36) and (5,40).

Under the assumption of additivity each dose of each combination is equivalent to a dose of ibuprofen, based on the relative potency ($\rho$) of diphenhydramine to ibuprofen obtained from the experiment on the first day. Thus, for example, in the dose ratio 19:8 the combination of 28 mg/kg of ibuprofen and 12 mg/kg of diphenhydramine is, under the assumption of additivity, equivalent to $(28+12\rho)$ mg/kg of ibuprofen. Table 3 shows for each dose of each of the combination doses tested the number of mice observed to be protected and the ibuprofen equivalent dose. For each of the four combination ratios, $ED_{50}$'s were estimated based on the observed number of mice protected at each ibuprofen equivalent dose using the method of Finney. Table 4 displays the estimated $ED_{50}$'s for each ratio.

RESULTS

The surprising synergistic effects of combining ibuprofen with diphenhydramine can be seen from the results of Tables 3 and 4 and the FIGURE of Drawing. The FIGURE of Drawing. summarizes all of the findings by depicting the $ED_{50}$'s obtained for each treatment alone, the $ED_{50}$ line if the treatments were additive, the number of mice/protected from writhing for each treatment studied and the estimated $ED_{50}$'s for each combination ratio.

The $ED_{50}$ of ibuprofen alone is estimated to be 24 mg/kg and for diphenhydramine to be 38 mg/kg. The relative potency of diphenhydramine to ibuprofen is 24/38. Among the 8 ratios tested on the second day, synergism appears to be present for four ratios, and these ratios were further investigated on days 3 and 4. The $ED_{50}$'s were found to be for the dosage ratio of 19:8, 23 mg/kg of ibuprofen, for the dosage ratio 6:28, 19 mg/kg of ibuprofen, for the dosage ratio 9:24, 18 mg/kg of ibuprofen, and for the dosage ratio 4:32, 23 mg/kg of ibuprofen. Two of these $ED_{50}$'s are substantially less than 24 mg/kg of ibuprofen which is the $ED_{50}$ that would be expected if the effects were additive. This represents a 25% reduction of the amount of ibuprofen that is required to obtain the effect in 50% of the animals. The graph in the Figure of Drawing indicates that many other dose ratios as well would produce an unexpected synergistic effect.

TABLE 1

NUMBER OF MICE PROTECTED AT TESTED DOSE LEVELS OF IBUPROFEN AND DIPHENHYDRAMINE

| Dose of Ibuprofen mg/kg | Dose of Diphenhydramine mg/kg | Number of Mice Protected | Number of Mice Not Protected |
|---|---|---|---|
| 2 | — | 0 | 8 |
| 5 | — | 0 | 8 |
| 10 | — | 1 | 7 |
| 20 | — | 3 | 5 |

TABLE 1-continued

NUMBER OF MICE PROTECTED AT TESTED DOSE LEVELS OF IBUPROFEN AND DIPHENHYDRAMINE

| Dose of Ibuprofen mg/kg | Dose of Diphenhydramine mg/kg | Number of Mice Protected | Number of Mice Not Protected |
|---|---|---|---|
| — | 5 | 1 | 7 |
| — | 10 | 2 | 6 |
| — | 20 | 3 | 5 |
| — | 40 | 4 | 4 |

TABLE 2

NUMBER OF MICE PROTECTED AT TESTED DOSES* OF THE COMBINATION OF IBUPROFEN AND DIPHENHYDRAMINE

| Dose of Ibuprofen mg/kg | Dose of Diphenhydramine mg/kg | Number of Mice Protected | Number of Mice Not Protected |
|---|---|---|---|
| 22 | 4 | 4 | 4 |
| 19 | 8 | 5 | 3 |
| 16 | 12 | 3 | 5 |
| 14 | 16 | 4 | 4 |
| 11 | 20 | 4 | 4 |
| 9 | 24 | 5 | 3 |
| 6 | 28 | 5 | 3 |
| 4 | 32 | 5 | 3 |

*Doses were chosen based upon $ED_{50}$'s of ibuprofen and diphenhydramine which under the assumption of additivity would provide protection for 50% of the mice.

TABLE 3

NUMBER OF MICE PROTECTED AT TESTED DOSE LEVELS OF FOUR DIFFERENT RATIOS OF DOSES OF IBUPROFEN TO DIPHENHYDRAMINE

| Combination Dose Ratio | Dose of Ibuprofen mg/kg | Dose of Diphenhydramine mg/kg | Ibuprofen Equivalent Dose Under Assumption of Additivity mg/kg | Number of Mice Protected | Number of Mice Not Protected |
|---|---|---|---|---|---|
| 19:8 | 8 | 3 | 9.9 | 1 | 7 |
| | 12 | 5 | 15.2 | 3 | 5 |
| | 16 | 7 | 20.4 | 2 | 6 |
| | 28 | 12 | 35.6 | 6 | 2 |
| 9:24 | 3 | 8 | 8.0 | 2 | |
| | 6 | 16 | 16.1 | 2 | 6 |
| | 12 | 32 | 32.2 | 6 | 2 |
| | 15 | 40 | 40.2 | 8 | 0 |
| 6:28 | 3 | 14 | 11.8 | 2 | 6 |
| | 4.5 | 21 | 17.7 | 3 | 5 |
| | 9 | 42 | 35.5 | 7 | 1 |
| 4:32 | 3 | 24 | 18.1 | 2 | 6 |
| | 3.5 | 28 | 21.1 | 3 | 5 |
| | 4.5 | 36 | 27.2 | 6 | 2 |
| | 5 | 40 | 30.2 | 6 | 2 |

TABLE 4

$ED_{50}$'s OF COMBINATION TREATMENTS IN IBUPROFEN EQUIVALENT DOSES

| Tested Combination Dose Ratios of Ibuprofen to Diphenhydramine | | Ibuprofen Equivalent $ED_{50}$ mg/kg |
|---|---|---|
| I | D | I |
| 100 | 0 | 24 |
| 19 | 8 | 23 |
| 9 | 24 | 18* |
| 6 | 28 | 19* |
| 4 | 32 | 23 |
| 0 | 100 | 24 |

*$ED_{50}$'s substantially less than 24 mg/kg, the dose that would be expected were the effects additive.

While the invention has been described and illustrated with reference to certain preferred embodiments thereof, those skilled in the art will appreciate that various changes, modifications and substitutions can be made therein without departing from the spirit of the invention. For example, effective dosages other than the preferred ranges set forth hereinabove may be applicable as a consequence of variations in the responsiveness of the mammal treated, severity of pain or inflammation, dosage related adverse effects, if any, observed and analogous considerations. Likewise, the specific pharmacological responses observed may vary depending upon the particular relative amounts of active components employed or whether same are used in combination with suitable pharmaceutical carriers, as well as the type of formulation and mode of administration employed, and such expected variations or differences in results are contemplated in accordance with the objects and practices of the present invention. It is intended, therefore, that the invention be limited only by the scope of the claims which follow.

What is claimed is:

1. A method for eliciting an enhanced analgesic and anti-inflammatory response in a mammalian organism in need of such treatment, comprising administering to such organism
   (i) an analgesically and anti-inflammatorily effective amount of pieroxicam, sudoxicam, isoxicam or CP-14,304, or a pharmaceutically acceptable salt thereof, and
   (ii) an analgesically and anti-inflammatorily potentiating amount of diphenhydramine.

2. The method as defined by claim 1, wherein the component (i) comprises an analgesically and anti-inflammatory effective amount of piroxicam.

3. The method as defined by claim 1, wherein the component (i) comprises an analgesically and anti-inflammatorily effective amount of sudoxicam.

4. The method as defined by claim 1, wherein the component (i) comprises an analgesically and anti-inflammatorily effective amount of isoxicam.

5. The method as defined by claim 1, wherein the component (i) comprises an analgesically and anti-inflammatorily effective amount of CP-14,304.

6. The method as defined by claim 1, comprising from about 10 to 20 mg of component (i).

7. The method as defined by claim 1, comprising from about 12.5 mg to 50 mg diphenhydramine.

8. The method as defined by claim 7, comprising from about 25 mg to 50 mg of diphenhydramine.

9. The method as defined by claim 1, wherein said composition is administered orally.

10. The method as defined by claim 1, wherein said component (i) is administered daily in divided doses.

11. The method as defined by claim 1, wherein said composition is administered orally at bedtime as an analgesically and anti-inflammatorily effective nighttime sleep aid.

12. A pharmaceutical composition of matter for eliciting an enhanced analgesic and anti-inflammatory response in a mammalian organism, said composition comprising:
(i) an analgesically and anti-inflammatorily effective amount of piroxicam, sudoxicam, isoxicam or CP-14,304, or a pharmaceutically acceptable salt thereof; and
(ii) an analgesically and anti-inflammatorily potentiating amount of diphenhydramine.

13. The pharmaceutical composition of matter as defined by claim 12, wherein the component (i) comprises an analgesically and anti-inflammatorily effective amount of piroxicam.

14. The pharmaceutical composition of matter as defined by claim 12, wherein the component (i) comprises an analgesically and anti-inflammatorily effective amount of sudoxicam.

15. The pharmaceutical composition of matter as defined by claim 12, wherein the component (i) comprises an analgesically and anti-inflammatorily effective amount of isoxicam.

16. The pharmaceutical composition of matter as defined by claim 12, wherein the component (i) comprises an analgesically and anti-inflammatorily effective amount of CP-14,304.

17. The pharmaceutical composition of matter as defined by claim 12, further comprising a non-toxic pharmaceutically acceptable inert carrier.

18. The pharmaceutical composition of matter as defined by claim 12, comprising from about 10 mg to about 20 mg of component (i).

19. The pharmaceutical composition of matter as defined by claim 12, comprising from about 12.5 mg to 50 mg diphenhydramine.

20. The pharmaceutical composition of matter as defined by claim 19, comprising from about 25 mg to 50 mg diphenhydramine.

21. The pharmaceutical composition of matter as defined by claim 12, comprising from about 10 mg to 20 mg piroxicam and about 12.5 mg to 50 mg diphenhydramine.

22. The pharmaceutical composition of matter as defined by claim 12, comprising from about 25 mg to 200 mg sudoxicam and about 12.5 mg to 50 mg diphenhydramine.

23. The pharmaceutical composition of matter as defined by claim 12, comprising from about 25 mg to 200 mg isoxicam and about 12.5 mg to 50 mg diphenhydramine.

24. The pharmaceutical composition of matter as defined by claim 12, comprising from about 25 mg to 200 mg CP-14,304 and about 12.5 mg to 50 mg diphenhydramine.

25. A composition of matter as defined by claim 12, said composition be adapted for oral administration.

26. A composition of matter as defined by claim 25, said composition being formulated as a tablet, capsule or elixir.

27. A composition of matter as defined by claim 25, said composition being adapted for oral administration sustained release form.

28. A composition of matter as defined by claim 12, said composition begin adapted for parenteral administration.

29. A composition of matter as defined by claim 28, said composition being formulated for intramuscular adminitration.

* * * * *